United States Patent
Vieira et al.

(10) Patent No.: US 8,758,457 B2
(45) Date of Patent: Jun. 24, 2014

(54) PROCESS FOR PRODUCING BIODIESEL

(75) Inventors: Jose Antonio Vidal Vieira, Rio de Janeiro (BR); Michele Sabba da Silva Lima, Rio de Janeiro (BR); Bruna Santiago Dias, Niteroi (BR); Carla de Araujo Ferreira, Rio de Janeiro (BR); Sonia Maria Cabral De Menezes, Rio de Janeiro (BR)

(73) Assignee: Petroleo Brasileiro S.A.—Petrobras, Rio de Janeiro ( * ) Notice: Subject to any disclaimer, the term of this patent is extended or adjusted under 35 U.S.C. 154(b) by 1099 days.

(21) Appl. No.: 12/064,203

(22) PCT Filed: Aug. 18, 2006

(86) PCT No.: PCT/GB2006/003110
§ 371 (c)(1),
(2), (4) Date: Aug. 18, 2009

(87) PCT Pub. No.: WO2007/020465
PCT Pub. Date: Feb. 22, 2007

(65) Prior Publication Data
US 2009/0320355 A1    Dec. 31, 2009

(30) Foreign Application Priority Data
Aug. 19, 2005    (BR) .................... 0503631

(51) Int. Cl.
| | |
|---|---|
| *C10L 1/19* | (2006.01) |
| *C07C 67/00* | (2006.01) |
| *C11C 3/00* | (2006.01) |
| *C11C 1/00* | (2006.01) |
| *C10G 3/00* | (2006.01) |
| *G01F 1/76* | (2006.01) |
| *C07C 67/03* | (2006.01) |
| *C07C 69/24* | (2006.01) |
| *C07C 69/52* | (2006.01) |
| *C10G 51/00* | (2006.01) |
| *C10G 99/00* | (2006.01) |
| *C10L 8/00* | (2006.01) |
| *C11C 3/12* | (2006.01) |

(52) U.S. Cl.
CPC . *C07C 67/00* (2013.01); *C11C 3/00* (2013.01); *C11C 1/00* (2013.01); *C10G 3/00* (2013.01); *G01F 1/76* (2013.01); *C07C 67/03* (2013.01); *C07C 69/24* (2013.01); *C07C 69/52* (2013.01); *B01J 2219/00006* (2013.01); *B01J 2219/32* (2013.01); *C10G 51/00* (2013.01); *C10G 99/00* (2013.01); *C10G 2300/1011* (2013.01); *C10G 2300/4081* (2013.01); *C10G 2300/70* (2013.01); *C10L 8/00* (2013.01); *C11C 1/002* (2013.01); *C11C 3/126* (2013.01); *Y02E 50/13* (2013.01)
USPC ............... 44/388; 44/437; 554/161; 554/163; 73/196

(58) Field of Classification Search
USPC ............ 44/437, 388; 554/167, 161, 168, 174; 73/861.355
See application file for complete search history.

(56) References Cited

U.S. PATENT DOCUMENTS

| | | | | |
|---|---|---|---|---|
| 5,354,878 | A * | 10/1994 | Connemann et al. | ......... 554/167 |
| 2004/0054206 | A1 | 3/2004 | Brunner et al. | |
| 2005/0204612 | A1* | 9/2005 | Connemann et al. | ........... 44/437 |

FOREIGN PATENT DOCUMENTS

WO    2004/029016 A    4/2004

*Primary Examiner* — Prem C Singh
*Assistant Examiner* — Chantel Graham
(74) *Attorney, Agent, or Firm* — Sughrue Mion, PLLC (57) ABSTRACT

A process for producing biodiesel from natural oils and/or fats, a low molecular weight $C_1$-$C_6$ alcohol and catalyst is described. The process preferably uses vegetable oils and is specifically configured for producing biodiesel from castor oil.

24 Claims, 3 Drawing Sheets

PROCESS FOR PRODUCING BIODIESEL

FIELD OF THE INVENTION

The present invention pertains to the field of processes for producing biodiesel from natural oils and/or fats, and more specifically vegetable oils such as castor oil, pine nut oil, soybean oil, cottonseed oil, rapeseed oil, sunflower oil, ouricury palm (*Cocos coronata*) oil, and/or any natural fats, and more specifically configured for producing biodiesel from castor seed oil.

BASIS OF THE INVENTION

The transesterification of vegetable oils to produce fatty acid esters is an ancient process with a broad range of industrial uses. In the 1980s and 1990s, this process was adapted for the production of an alternative fuel to diesel. The basic requirements of the new processes are high purity and yield. These objectives have been fully achieved, but only when the raw materials are methanol and non-hydroxylated vegetable oils, with rapeseed and soybean oil being the most used.

In Brazil, due to regional peculiarities, there is considerable government interest in developing a specific process for the production of biodiesel from castor oil. However, since this oil possesses particular characteristics due to the presence of a hydroxyl group in its molecular structure, the conventional processes do not produce good results. This has necessitated research and development of a process specially adapted to the transesterification of castor oil.

Additionally, in Brazil there is also enormous interest in replacing methanol with ethanol, which introduces great complexity into the process, especially when the oil selected for the transesterification reaction is castor oil, due to the fact that both raw materials have hydroxyl groups in their molecular structures. Moreover, ethanol is not used in any industrial biodiesel plant outside Brazil, and in no high capacity plant, even in Brazil.

U.S. Pat. No. 4,608,202 describes a process for producing fatty acid esters of short-chain aliphatic alcohols by catalytic transesterification of natural fats and/or oils containing free fatty acids (oil phase), with the corresponding monoalcohols. The oil phase is submitted to preliminary esterification with the monoalcohols in the presence of acid esterification catalysts at a temperature no greater than 120° C. under pressures no greater than 5 bars and in the presence of a liquid entraining agent substantially immiscible with the oil phase, after which the reaction product is separated into an entraining agent phase containing the acid catalyst and water of reaction and the treated oil phase, the oil phase is subjected to transesterification while the acidic catalyst-containing entraining agent phase is returned, after partial drying, to the preliminary esterification step. By this process, fats and/or oils with acid numbers of up to 60 can be processed in the preliminary esterification step to give an oil phase having a low acid number.

U.S. Pat. No. 4,652,406 discloses producing fatty acid esters by catalytic esterification of natural oils and fats. Initially the free fatty acids are reacted, for example, with methanol in the presence of an acid catalyst at 50-120° C. and atmospheric pressure. The resulting mixture separates in two phases: (1) an alcoholic phase containing the acid catalyst and part of the water of reaction; and (2) an oil phase. The phases are recovered separately. The oil phase is then extracted with an extractant, preferably immiscible, which comprises a mixture of glycerol and methanol, to remove the residual water of reaction. In the final step, the extracted oil phase is transesterified with a $C_1$-$C_4$ alkanol, in the presence of an alkaline catalyst at substantially atmospheric pressure.

U.S. Pat. No. 4,695,411 discloses a process for preparing a composition of fatty acid esters useful for diesel engines, wherein the composition contains at least one hydrated ethyl alcohol. Step (A) consists of acid transesterification in the presence of a hydrated alcohol such as ethyl alcohol containing 1 to 60% by weight of water, producing glycerol and ethyl esters; step (B) consists of reducing the free acidity of the ester phase, and step (C), the basic esterification of the phase resulting from phase B in the presence of a monoalcohol with 1 to 5 carbon atoms, and recovery of the ester phase.

U.S. Pat. No. 5,354,878 discloses a process for producing higher fatty acid alkyl esters from an oil phase and lower alcohols by catalytic esterification at temperatures up to 100° C. in the presence of an alkaline catalyst, which includes: a) introducing a mixture of oil phase, alcohol and catalyst at reaction temperature into the top of a first reactor column, at a rate of flow which is lower than the rate of separation of glycerine from the reaction mixture; b) passing the reaction mixture to a second reactor for additional transesterification; c) the reaction mixture thus obtained is additionally freed of glycerine in an initial separation step by a short duration wash; d) the reaction mixture is passed to a third reactor with additional alcohol and catalyst, and at a flow rate conforming to the first step of the process; e) the reaction mixture is additionally transesterified; f) the reaction product is freed from the remaining methanol, glycerine, the soaps formed and catalyst in a second separation step, through the addition of an aqueous extraction buffer solution; and g) the reaction mixture is freed of primary alcohols by rectification, washed with suitable extraction and washing solutions, and dried.

U.S. Pat. No. 5,434,279 discloses a process for esterification in various steps for oils and fats, including oils used such as those for frying, which comprises of the addition, after the second step is finished, of at least part of the glycerine from the first step; the glycerine is separated again, and the fatty acid ester is separated from the excess alcohol or diol and acidified. It is claimed that the process results in a highly pure fatty acid ester.

Brazilian Application PI0404243-3A discloses a process for producing biodiesel from semi-refined vegetable oil, anhydrous alcohol and an alkaline catalyst. The process is in two steps, with a temperature of 60-80° C. The reagents are mixed in a first reactor, and after allowing time for reaction the products formed are sent to a first evaporator to separate the non-reacted alcohol, with the alcohol being recovered in a condenser. The residues of oil, biodiesel and glycerine are cooled and sent to a first centrifugal separator for separation, under an inert atmosphere, of the glycerine from the residual oil and biodiesel. The biodiesel formed and the residual oil are then reacted with more anhydrous alcohol and alkaline catalyst by mixing in a second continuous mixer. After mixing, the mixture is heated and passed to a second reactor, where the reaction occurs, and the product then receives a dose of hydrochloric or sulphuric acid to deactivate the alkaline catalyst; the alcohol is separated in an evaporator, and the product proceeds to a second centrifuge for separation of the glycerine and biodiesel. The product is washed in water lightly acidified with citric acid in sufficient quantity to react with residual soaps, and the washing water then separated in a washing centrifuge. The washed biodiesel is sent to a vacuum dryer, cooled and then stored. Certain aspects of the technology described in this Brazilian application could affect the economic viability of the same. Moreover, the process is not designed for the specific features of castor oil.

In general, the processes used worldwide in industrial plants for producing biodiesel were not developed for use with castor oil and/or have not even been tested, or simply do not work with this raw material.

The processes described in the scientific literature and in patents either do not use recycling or merely recycle the dense phase from the final reaction step to the first reaction step, or they react the ester phase from the second reaction step with part of the glycerine from the first reaction step. The steps of the reaction are sequential, that is the product of the first step is the starting material of the second, with the possibility of a further step, also sequential. By contrast, the reaction flow proposed in this invention uses 'parallel' steps, optimizes recycling flow, and allows better re-utilization of the residual catalyst, minimizing consumption of the catalyst.

Another distinctive aspect of the invention is the fact that the processes of the state of the art mix the dense phases from the reactions with the aqueous phases from washing. Subsequently, after neutralizing the excess catalyst and recovering the residual alcohol, the water has to be evaporated off in order to concentrate the glycerine to 85%. The present invention, on the other hand, establishes technical conditions that allow the aqueous fractions to be processed separately, whenever it is economically advantageous to do so. Such flexibility also makes it possible to limit the treatment to the minimum necessary for the disposal of the aqueous effluents, if the level of glycerine or of alcohols (depending on the method chosen for alcohol recovery) does not economically justify the costs of the treatment. Opting for separate treatment enables the removal of a large part of the glycerine produced in the form of a highly concentrated fraction that requires only distillation of the residual alcohol and neutralization of excess catalyst (not necessarily in this order), which is minimized in the present process. The soap may or may not be converted into fatty acid, depending only on the existence of a local market for the fatty acids. Due to the fact that these glycerine fractions contain less soap and catalyst, the final level of saline impurities in the glycerine product is also lower.

The industrial processes most used in the art for biodiesel production use steps of neutralization, washing with water and vacuum drying for purifying the final product. The proposed process, however, presents an alternative use for one of the dense phase fractions generated in the process itself to increase the recovery of catalyst by returning part of this fraction to the process. Although the aim is to minimize the consumption of catalyst, the process of the invention also reduces the level of contaminants in the crude biodiesel fraction, facilitating the washing process and reducing the consumption of water and acid used in neutralization.

In addition, the present invention also presents an alternative use of glycerine to extract a large part of the excess alcohol before the step of washing the biodiesel, and later recovery by evaporation of the alcohol absorbed in the glycerine. This alternative is particularly interesting when the alcohol used in the transesterification is ethanol, since it minimizes the water content of the recovered alcohol and the cost of dehydration.

Therefore, there is still a need in the art for a process for obtaining biodiesel by transesterification of natural oils and/or fats and, more specifically, of castor oil, in the presence of a transesterification catalyst, wherein this process includes a step (a) in which virgin and/or recycled oil and/or fat are/is made to react with a low molecular weight primary alcohol and a catalyst, followed by (b) separation of the dense phase produced during step (a), containing a high glycerine content, a step (c) in which the reactants are virgin and/or recycled oil/fat, the low molecular weight primary alcohol and the dense phases separated in steps (b) and (f) plus part of the dense phase resulting from the extraction carried out in step (g), followed by (d) separation of the dense phase produced during step (c), with a high glycerine content (added plus produced), a step (e) in which the reactants are the light phases obtained after separation in steps (b) and (d), the low molecular weight primary alcohol and the transesterification catalyst, followed by (f) separation of the dense phase produced during step (e), with a high glycerine content, and an alternate step (g) of extracting the excess catalyst contained in the light phase obtained after separation in step (f), through contact with the dense phase separated in step (d), and additional steps for purification and finishing, as well as treatment of effluents and recovery of glycerine, alcohol and fatty acids, with flexibility to suit the economics of the recovery process to the various kinds of raw materials, alcohols and catalysts, and including options to minimize the moisture content of the recovered alcohol, and such a process is described and claimed in the present application.

SUMMARY OF THE INVENTION

Broadly speaking, the process of the invention for producing biodiesel from natural oils and/or fats in the presence of a transesterification catalyst includes various processing steps, which to facilitate understanding can be grouped into three distinct sections: a Reaction Section, in which the transesterification reactions take place; a Purification Section, where the impurities resulting from the production process are removed; and a Section for Recovering Alcohols, Glycerine and Fatty Acids. In the Reaction Section, the following steps of the process are carried out:

a) First reaction step (MR-1A), in which the reactants are virgin and/or recycled oil and/or fat, a low molecular weight primary alcohol and a transesterification catalyst, giving fatty acid esters and glycerine;

b) Separation of the dense phase produced during step (a), this phase having a high glycerine content and a very low water content;

c) New initial reaction step (MR-1B), in which the reactants are virgin and/or recycled oil and/or fat, a low molecular weight primary alcohol and the dense phases (previously submitted to separation of solids) produced in reaction steps MR-1A and MR-2, and, optionally part of the dense phase resulting from the extraction operation in step (g);

d) Separation of the dense phase produced during step (c), which has a high glycerine content;

e) Second reaction step (MR-2), in which the reactants are the light phases of reaction steps MR-1A and MR-1B, a low molecular weight primary alcohol and a transesterification catalyst;

f) Separation of the dense phase produced during step (e), which has a high glycerine content and a very low water content;

g) Alternatively, extraction of the residual catalyst contained in the light phase of reaction step MR-2, through contact with the dense phase separated from reaction step MR-1B, the dense phase having previously been submitted to the evaporation of excess alcohol, or otherwise;

h) Neutralization of the remaining dense phase fractions; and i) Evaporation of the excess alcohol, especially from the fraction separated in step (d), whereby a product with a high concentration of glycerine is obtained, and levels of contaminants lower than those produced in the processes of the state of the art for homogenous catalysis.

The crude biodiesel produced is then sent to the Purification Section, where it is submitted to a process of purification and finishing that comprises:

a) When the catalyst used is of the basic type, an optional step of partial or total neutralization of the residual alkalinity in the biodiesel from steps (f) and (g) in the Reaction Section, by adding acidified or pure water, followed by separation of the resulting dense phase;

b) Various stages of washing of the biodiesel fraction from step (a) with pure water or in counter current, until complete removal of residual contaminants soluble in water, such as soaps, salts, glycerine and alcohols;

c) Drying of the washed biodiesel fraction; and d) Depending on the oil or fat used as raw material, removal of waxes and other substances separable by cooling, to suit the plugging point to local specifications.

A second alternative for the purification and finishing of the biodiesel comprises the following steps:

a) When a basic-type catalyst is used, neutralization of the residual alkalinity in the biodiesel from steps (f) or (g) in the Reaction Section, through the controlled addition of an alcoholic solution of an acid, which preferably, but not necessarily, has a low ionization constant;

b) Distillation or total or partial evaporation of the alcohol contained in the biodiesel fraction, followed by separation of the resulting dense phase;

c) Washing of the biodiesel fraction from step (b) with pure water or in counter current, until the complete elimination of the residual water-soluble contaminants, such as soaps, salts, glycerine and alcohols;

d) Drying of the washed biodiesel fraction; and e) Depending on the oil or fat used as raw material, removal of waxes and other substances separable by cooling, to suit the plugging point to local specifications.

A third alternative for the Purification Section involves purification and finishing of biodiesel produced by means of any reaction configuration, either a conventional configuration or those of the present invention, but especially for biodiesel produced with ethanol, which can be carried out via the following steps:

a) When a basic-type catalyst is used, neutralization of the residual alkalinity in the biodiesel from steps (f) or (g) in the Reaction Section, by means of the controlled addition of an alcoholic solution of an acid, preferably, but not necessarily, of a low ionization constant;

b) Before or after the neutralization of the biodiesel described in step (a) above, extraction of the excess alcohol with a pre-evaporated glycerine fraction (low level of alcohol), in order to minimize or eliminate a later step of evaporating the alcohol in the biodiesel. A glycerine phase enriched with alcohol is forwarded to a special alcohol recovery section, by means of evaporation or distillation under conditions that favour minimization of the water content in the recovered alcohol. The glycerine is then either totally or partially returned to the extraction system;

c) Optionally, evaporation/distillation of the residual alcohol still contained in the biodiesel fraction, followed by physical separation of the resulting dense phase;

d) Washing of the biodiesel fraction resulting from step (a), (b) or (c), according to the sequence chosen, with pure water or in counter current, until the complete elimination of the residual water-soluble contaminants, such as soaps, salts, glycerine and alcohols;

e) Drying of the washed biodiesel fraction; and f) Depending on the oil or fat used as raw material, removal of the waxes and other substances by cooling, to suit the plugging point to local specifications.

The dense phases separated in the Reaction and Purification Sections, containing glycerine, alcohols, catalyst residues, soaps and salts, are forwarded to the Recovery Section for Alcohols, Glycerine and Fatty Acids, where these products are recovered, in accordance with the economic benefits of the process, which in turn depend on the local market value for these products.

The present invention offers flexibility, depending on economic conditions and the type of raw material (oil or fat, alcohol and catalyst) used, for various alternative structures for the steps in the Recovery Section for Alcohols, Glycerine and Fatty Acids. Thus, glycerine-rich fractions can be treated together with the water-rich fractions, or not; fatty acids can be recovered or not; the aqueous fractions can go through the recovery steps or be treated only for disposal purposes, etc.

Within the many possibilities, some basic steps are described below, not necessarily in order of sequence:

a) Neutralization of excess catalyst;

b) Recovery of residual alcohols by evaporation/-distillation;

c) Acidification, to transform soaps into fatty acids, with subsequent separation of the light phase, rich in fatty acids; and d) Neutralization of the glycerine-rich phase and concentration of the glycerine to the desired concentration by evaporating excess water.

With the option of recovering glycerine from the aqueous fractions, disposal of aqueous effluents becomes minimal or non-existent, due to the recovery of the water used for washing during the glycerine concentration phase.

The invention thus offers a process for producing biodiesel by transesterification of natural oils and/or fats wherein use is made of dense phase fractions produced within the process itself in order to minimize catalyst consumption.

The invention also offers a process for producing biodiesel by transesterification of natural oils and/or fats which offers a reduction in the level of contaminants in the crude biodiesel fraction, facilitating the purification process and reducing the consumption of water and acid used for neutralization.

In addition the invention offers a process for producing biodiesel by transesterification of natural oils and/or fats, wherein a highly concentrated glycerine fraction is obtained, exceeding the specifications for crude glycerine, containing less soap and catalyst, with an equally minimized final level of salt impurities.

The invention also offers a process for recovering excess alcohol (used for biodiesel production) with a low water content, reducing the cost of reusing the same.

The invention also offers a process which allows for flexibility in deciding to what extent it is advantageous to recover residual quantities of glycerine and alcohols contained in the washing effluents, minimizing consumption of energy and the cost of treating aqueous effluents.

DETAILED DESCRIPTION OF THE PREFERRED EMBODIMENTS

The invention discloses a process for producing biodiesel from vegetable oils and animal fats, typically castor oil, and low molecular weight alcohols in the presence of a transesterification catalyst, typically acidic or basic, by suitable combination of a series of single operations, operational conditions and process design.

The process comprises three reaction steps, two of them in parallel, (R-1A) and (R-1B), using oil as the starting material and one in series (R-2) which uses as starting material the biodiesel-rich phases generated in the previous steps, (R-1A) and (R-1B). In addition, one of the two first two reaction steps, (R-1B), reuses the catalyst used in the other steps.

In the process of the invention, the conditions are as follows: ambient temperature$\leq T \leq 140°$ C.; atmospheric pressure$\leq P \leq 10$ bar, and $3 \leq$ molar ratio (low molecular weight alcohol/vegetable oil or animal fat)$\leq 30$, and preferably $4 \leq$ molar ratio (low molecular weight alcohol/vegetable oil or animal fat)$\leq 10$.

The ideal temperate, pressure and proportion of reactants will depend on the fatty acid composition in the raw materials used. For example, castor oil which contains from 85 to 90% wt of ricinoleic acid requires specific conditions of reaction as a function of the specific physical chemical properties of castor oil.

The castor or other vegetable oil or animal fat used should preferably have a free fatty acid content of less than 5% wt, more preferably less than 0.5% wt, and most preferably less than 0.1% wt, and preferably an acid value less than 10 mg KOH/g, more preferably less than 1 mg KOH/g and most preferably less than 0.2 mg KOH/g.

The moisture content of the oil or fat should preferably be less than 0.8% wt, more preferably less than 0.2% wt and most preferably less than 0.1% wt.

The catalyst may be either of the acid or basic type, but is preferably of the basic type and more preferably constituted by sodium or potassium hydroxide or by sodium or potassium methoxide or sodium or potassium ethoxide; and it is preferably used in the proportion of 0.1% to 2.5% by weight relative to the oil or fat.

If a basic catalyst is used in the trans-sterification reaction, the neutralizing agent can be any organic or inorganic acid, strong or weak, concentrated or dilute, aqueous or alcoholic, provided that the turning point of neutralization of the catalyst is carefully controlled. Optionally, to facilitate control, acid buffers in the desired pH range can be used. The acids preferably comprise hydrochloric, sulphuric, phosphoric, acetic and/or citric acid.

The low molecular weight primary alcohol is an alcohol in the range $C_1$-$C_6$. The most preferred is ethyl or methyl alcohol, used in the proportions indicated above. The process also allows the use of mixtures of alcohols, provided that the molar ratios (mixture of low molecular weight alcohols/vegetable oil or animal fat) are maintained as specified.

The preferred embodiments of the invention will be described below with reference to the attached drawings.

It should be made clear that the drawings do not indicate all of the possible arrangements of the process covered by the present invention.

Figure 1:
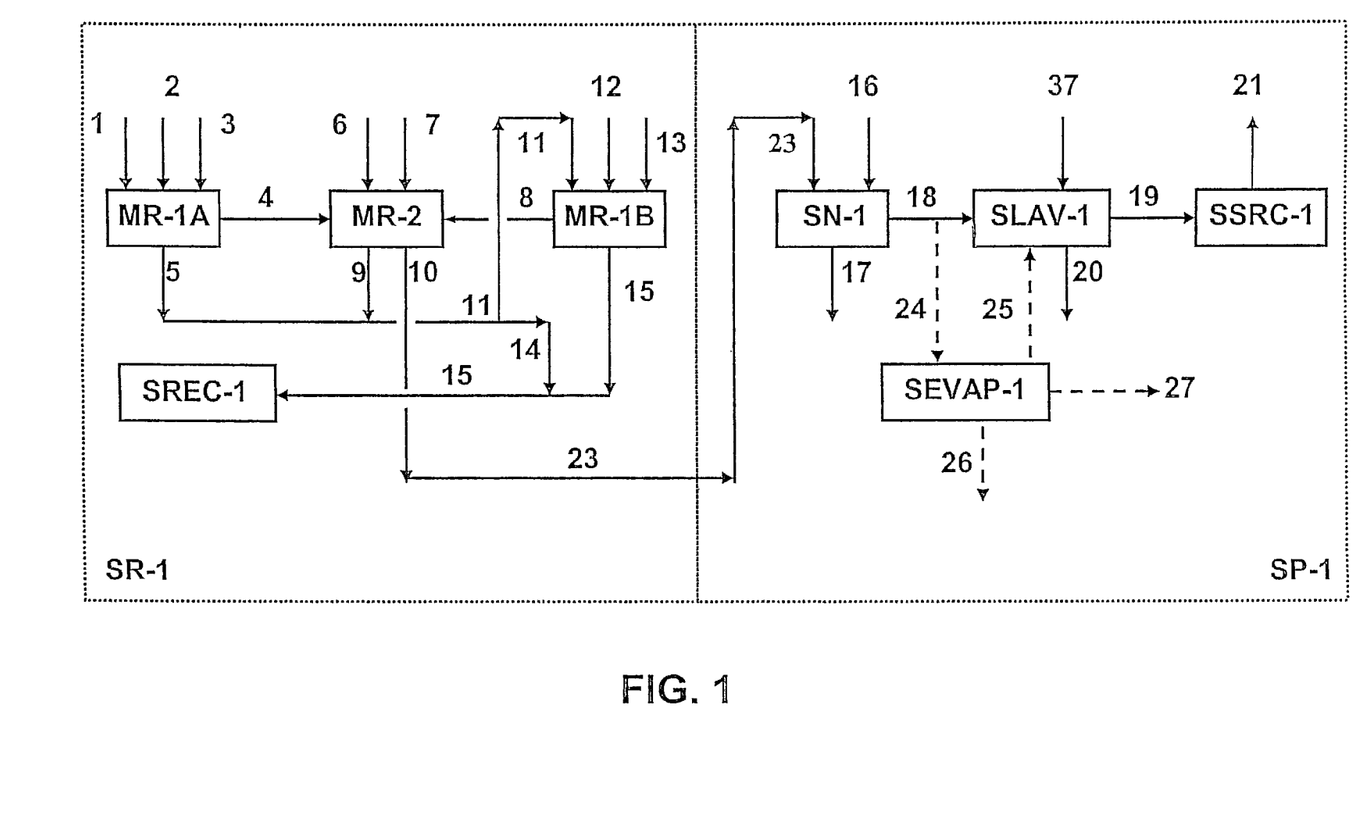
FIG. 1, attached, is a flow diagram showing a first alternative configuration of the process of the invention, considering continuous operation.

In FIG. 1, the reaction modules (MR-1A), (MR-1B), and (MR-2) are sets of equipment which function, at least, as mixers, reactors, separators, heat exchangers and pumps; the present invention is not limited to any particular models for these items of equipment.

For a better understanding and description of the process, the flow diagram in FIG. 1 can be divided into two sections: a Reaction Section (SR-1) and a Purification Section (SP-1). The starting materials for the process, comprising oil or fat (1), alcohol (2) and catalyst (3), are fed to reaction module (MR-1A), in the ideal proportions and at the ideal temperatures for the type of raw materials used. As they pass through the reaction module (MR-1A) these materials are mixed, reacted and separated into a dense phase (5) and a light phase (4) both formed during the reaction.

Simultaneously, fresh oil or fat (12) and alcohol (13) are fed to a reaction module (MR-1B), to which is also fed a fraction (11) constituted totally or partially of the dense phases (5) and (9) separated in the reaction modules (MR-1A) and (MR-2).

The three are supplied to the reaction module (MR-1B), regulated to the ideal proportions and temperature, and mixed, reacted, and separated into a dense phase, (15), and a light phase, (8), both formed during the reaction.

The light phases separated in reaction modules (MR-1A), (4), and (MR-1B), (8), are forwarded to reaction module (MR-2), together with fresh alcohol (6) and catalyst (7). These four, previously regulated to the ideal proportions and temperature, are mixed, reacted, and separated into a dense phase (9) and light phase (10), formed during the reaction.

The totality of the light phase (10) thus separated, constituted by biodiesel, excess alcohol and catalyst, soaps and impurities, is sent as (10) and (23) to the Purification Section (SP-1).

The dense phase separated in reaction module (MR-2) is withdrawn as (9), and is united with the dense phase (5) separated in reaction module (MR-1A) to give (11), which is fed to reaction module (MR-1B). This fraction (11) enables the catalyst to be reused. The dense phase (15) separated in reaction module (MR-1B), (15), and the excess (if any) of the other dense phases (14) pass to the Section for Recovering Alcohols, Glycerine and Fatty Acids (SREC-1).

In the Purification Section (SP-1), the light phase (23) is forwarded to a neutralization system (SN-1), where it is subjected to reaction with a neutralizing agent (16) and separation of the dense phase (17) and light phase (18) products of neutralization. The light phase, still constituted by crude, but neutralized, biodiesel, passes to the washing system (SLAV-1) as (18) and the dense phase (17) is sent to the Section for Recovering Alcohols, Glycerine and Fatty Acids (SREC-1).

The washing system (SLAV-1) also receives fresh water (37), the function of which is to remove water-soluble contaminants in the biodiesel, such as soaps, salts, alcohols, catalyst residues and glycerine. After close contact of the two currents, counter current or otherwise, for various stages, the biodiesel is separated as a light phase and forwarded as (19) to the drying and wax removal section (SSRC-1). The aqueous phase thus separated (20) is sent to the Section for Recovering Alcohols, Glycerine and Fatty Acids (SREC-1).

Alternatively, before washing the crude biodiesel can be submitted to a step of evaporation or distillation of excess alcohol in order to decrease the costs of dehydrating the alcohol after recovery. In this option, the neutralized biodiesel, as (18) and (24), is sent to the alcohol evaporation/distillation system (SEVAP-1), where all or a large part of the alcohol content therein is removed and forwarded to the Section for Recovering Alcohols, Glycerine and Fatty Acids (SREC-1) as (27). After removing the alcohol, a dense phase rich in glycerine is separated, also in the alcohol evaporation/distillation system (SEVAP-1), and forwarded as (26) to the Section for Recovering Alcohols, Glycerine and Fatty Acids (SREC-1). The semi purified biodiesel then passes as (25) to the washing system (SLAV-1).

Washed biodiesel which enters the drying and wax removal section (SSRC-1) as (19) is dried, preferably under heat and vacuum, under pressure and temperature controlled in accordance with the type of oil or fat used as the starting materials, followed by cooling and separation of waxes and other high-melting point compounds.

In the case of methyl biodiesel from castor oil, simple cooling to ambient temperature, followed by decantation for a few days, already enables the separation of a considerable proportion of solids. The degree of removal of wax and of other high-melting point compounds will depend on the specification for the plugging point desired in the final product. This product leaves the drying and wax removal section (SSRC-1) as (21) to tank storage.

The dense phases sent to the Section for Recovering Alcohols, Glycerine and Fatty Acids (SREC-1) as (15), (17), (20), (26) and (27) enter this section at specific points, depending on their water contents and the decision as to the type of recovery to be adopted, such as, for example, mixing or treating the aqueous phases separately, recovering all of the glycerine from the aqueous phases or treating them only for disposal, and dehydrating the alcohol recovered or selling it as hydrated alcohol (when the process uses ethyl alcohol), etc.

In the diagram in FIG. 2, the configuration of the Purification Section (SP-1) is the same as in FIG. 1, with some alternative steps added to the configuration of the Reaction Section (SR-2), as detailed below.

Figure 2:
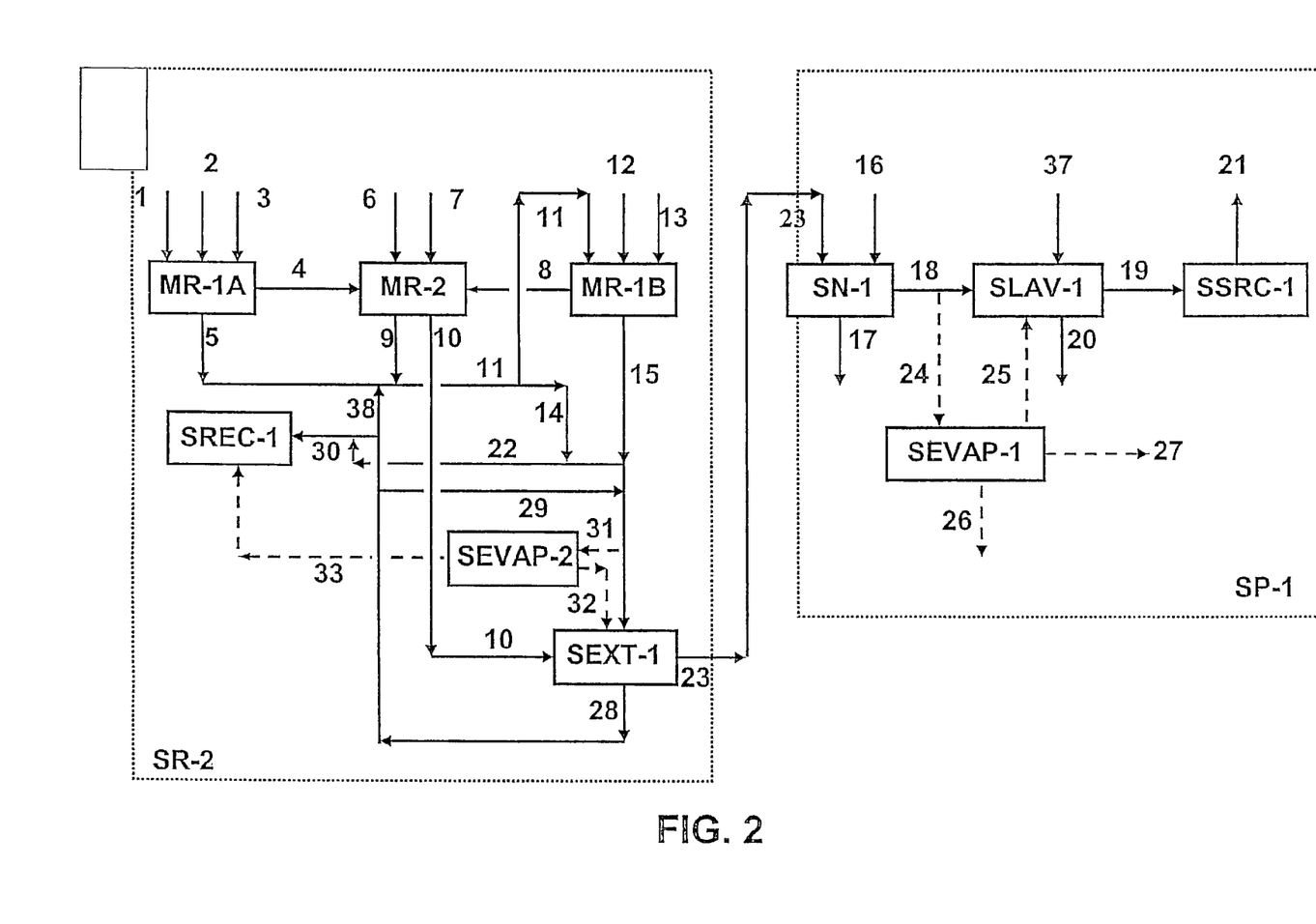
FIG. 2, attached, is a flow chart showing an alternative configuration for the process of the invention, with one or two additional stages to increase recovery of the catalyst and/or alcohol.

The diagram in FIG. 2 presents process and equipment configurations similar to those in FIG. 1, with the addition of alternatives intended to minimize contamination by water of the alcohol recovered and thus decrease the cost of purifying the alcohol recovered.

The starting materials for the process, constituted by oil or fat (1), alcohol (2) and catalyst (3), are fed to reaction module (MR-1A) in the ideal proportions at the ideal temperatures for the starting materials employed. As they pass through the reaction module (MR-1A) these materials are mixed, reacted and separated into a dense phase (5) and light phase (4), both formed during the reaction. Simultaneously, fresh oil or fat (12) and catalyst (13) are fed to reaction module (MR-1B), to which is also fed (11), constituted totally or partially of the dense phases (5), (9) and (38) from reaction modules (MR-1A) and (MR-2) and the residual catalyst extraction system (SEXT-1). As in FIG. 1, (11) enables reuse of the catalyst in the configuration in FIG. 2.

The three are supplied to reaction module (MR-1B) regulated to the ideal proportions and temperature, and mixed, reacted, and separated into a dense phase, (15), and light phase, (8), both formed during the reaction. The light phases (8) separated in reaction modules (MR-1A), (4), and (MR-1B), (8), are then forwarded to reaction module (MR-2), together with fresh alcohol (6) and catalyst (7). These four, previously regulated to the ideal proportions and temperatures, are mixed, reacted, and separated into a dense phase (9) and light phase (10) both formed during the reaction.

The light phase thus separated, constituted by biodiesel, excess alcohol and catalyst, soaps and impurities, leaves the reaction module (MR-2) as (10), and passes to the residual catalyst extraction system (SEXT-1).

The dense phase separated in reaction module (MR-2) is withdrawn as (9), and is united with the dense phase (5) separated in reaction module (MR-1A) and with the dense phase (38) from the residual catalyst extraction system (SEXT-1), to give (11), which is fed to reaction module (MR-1B).

The dense phase separated in reaction module (MR-1B) is withdrawn as (15), and is united with the recycled dense phase (29), which is fed back to the residual catalyst extraction system (SEXT-1) to promote extraction of part of the excess catalyst retained in the biodiesel-rich phase (10) leaving reaction modules (MR-2). This operation is carried out with one, two or three theoretical stages of intimate contact between the phases within the residual catalyst extraction system (SEXT-1).

After extraction, the biodiesel-rich phase (23) passes to the Purification Section (SP-1), where it is subjected to the same processing steps described in FIG. 1.

The glycerine-rich phase (28) is divided into three fractions (29), (30) and (38).

Fraction (29) is recycled to the residual catalyst extraction system (SEXT-1), in order to complete the inventory necessary for extraction.

Fraction (38) is united with the other fractions rich in residual catalyst which make up (11), which supplies reaction module (MR-1B) with recovered catalyst. The size of this fraction depends on the content of catalyst to be recovered in the residual catalyst extraction system (SEXT-1).

Finally, fraction (30) closes the cycle, discharging glycerine produced within the totality of the process in the Section for Recovering Alcohols, Glycerine and Fatty Acids (SREC-1).

Fraction (22) aids in closing the cycle by discharging into (30) the excess dense phase not used in reaction module (MR-1B) or in the residual catalyst extraction system (SEXT-1).

Alternatively, (15) can be rerouted to the alcohol evaporation/distillation system (SEVAP-2) via (31), where excess alcohol is removed and forwarded to the Section for Recovering Alcohols, Glycerine and Fatty Acids (SREC-1) as (33). Removal of excess alcohol gives a product rich in glycerine, which is passed as (32) to the residual catalyst extraction system (SEXT-1) and then follows the process flow described above.

Figure 3:
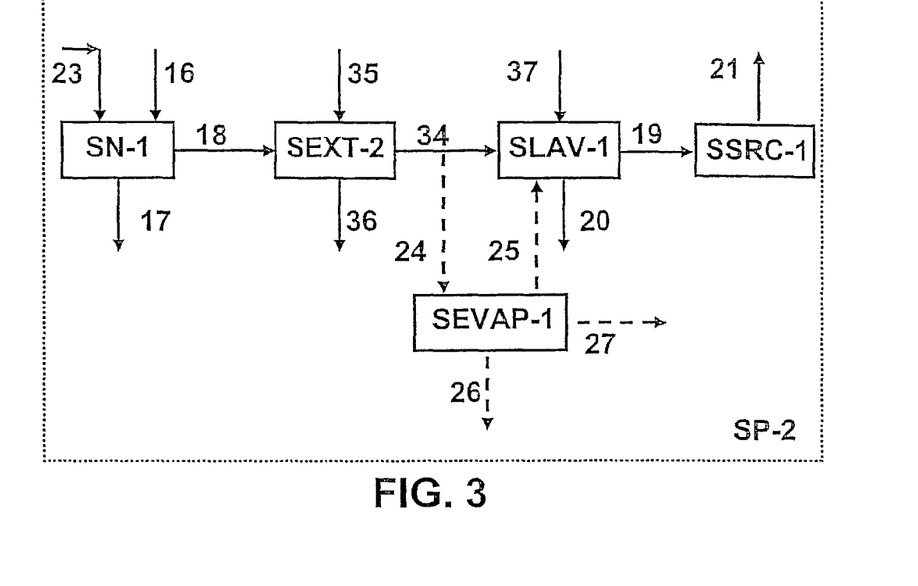
FIGS. 3 and 4, attached, are flow diagrams showing alternative configurations of the process for the biodiesel purification steps, applicable to any reaction configuration, either a conventional configuration or those of the present invention.

The diagram in FIG. 3 only considers alternatives in the process for the Purification Section (SP-2), which can be used with the configurations of Reaction Section (SR-1) or Reaction Section (SR-2) or with configurations traditionally adopted for reactions producing biodiesel.

In the Purification Section (SP-2), crude biodiesel (23), which can be produced by any process with an acid or basic catalyst, is forwarded to a neutralization system (SN-1), where it is subjected to reaction with a neutralizing agent (16) and separation of the dense phase (17) and light phase (18) products of neutralization. The light phase (18), still constituted by crude, but neutralized, biodiesel, passes to the alcohol extraction system (SEXT-2), and the dense phase (17) is sent to the Section for Recovering Alcohols, Glycerine and Fatty Acids (SREC-1) (not shown).

The alcohol extraction system (SEXT-2) also receives recovered glycerine (35) from the Section for Recovering Alcohols, Glycerine and Fatty Acids (SREC-1), to promote extraction of part of the excess alcohol retained in (18), thereby preventing this alcohol from entering into contact with washing water in the washing system (SLAV-1) and becoming hydrated. This operation is carried out in one, two, three or four theoretical stages of intimate contact between the phases within the alcohol extraction system (SEXT-2). The dense phase which is separated, (36), which is rich in glycerine and alcohol with a low moisture content, passes to the Section for Recovering Alcohols, Glycerine and Fatty Acids (SREC-1) in the anhydrous or semi-anhydrous form.

After extraction, the biodiesel-rich phase (34) passes to the washing system (SLAV-1), which also receives fresh water (37), the function of which is to remove water-soluble contaminants in the biodiesel, such as soaps, salts, alcohols, catalyst residues and glycerine. After close contact of the two currents, counter current or otherwise, for various stages, the biodiesel is separated as a light phase and forwarded as (19) to the drying and wax removal section (SSRC-1). The aqueous phase thus separated (20) is sent to the Section for Recovering Alcohols, Glycerine and Fatty Acids (SREC-1).

Alternatively, before washing the crude biodiesel can be submitted to a step of evaporation or distillation of excess alcohol in order to decrease the costs of dehydrating the alcohol after recovery. In this option, the neutralized biodiesel, as (34) and (24), is sent to the alcohol evaporation/distillation system (SEVAP-1), where all or a large part of the alcohol content therein is removed and forwarded to the Section for Recovering Alcohols, Glycerine and Fatty Acids (SREC-1) (not shown) as (27). After removing the alcohol, a dense phase rich in glycerine is separated, also in the alcohol evaporation/distillation system (SEVAP-1), and forwarded as (26) to the Section for Recovering Alcohols, Glycerine and Fatty Acids (SREC-1). The semi purified biodiesel then passes as (25) to the washing system (SLAV-1) for final washing.

Washed biodiesel which enters the drying and wax removal section (SSRC-1) as (19) is dried, preferably under heat and vacuum, under pressure and temperature controlled in accordance with the type of oil or fat used as the starting materials, followed by cooling and separation of waxes and other high-melting point compounds.

In the case of methyl biodiesel from castor oil, simple cooling to ambient temperature, followed by decantation for a few days, enables the separation of a considerable proportion of solids. The degree of removal of wax and of other high-melting point compounds will depend on the specification for the plugging point desired in the final product. This product leaves the drying and wax removal section (SSRC-1) as (21) to tank storage.

The dense phases (17), (20), (26), (27) and (36) sent to the Section for Recovering Alcohols, Glycerine and Fatty Acids (SREC-1) enter this section at specific points, depending on their water contents and the decision as to the type of recovery to be adopted, such as, for example, mixing or treating the aqueous phases separately, recovering all of the glycerine from the aqueous phases or treating them only for disposal, and dehydrating the alcohol recovered or selling it as hydrated alcohol (when the process uses ethyl alcohol), etc.

Figure 4:
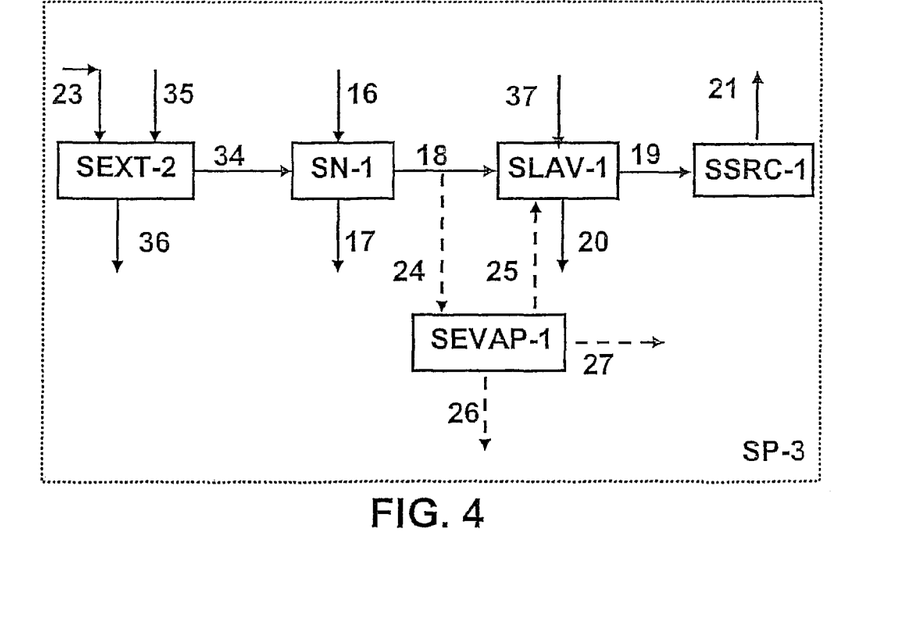

The diagram in FIG. 4 considers an alternative process for the Purification Section (SP-3) similar to that in FIG. 3, differing only in inverting the sequence of the neutralization system (SN-1) and the alcohol extraction system (SEXT-2).

This purification flow can also be used with the configurations of Reaction Section (SR-1) or Reaction Section (SR-2) or with configurations traditionally adopted for reactions producing biodiesel.

In the Purification Section (SP-3), crude biodiesel (23), which can be produced by any process with an acid or basic catalyst, is initially sent to the alcohol extraction system (SEXT-2), which also receives recovered glycerine (35) from the Section for Recovering Alcohols, Glycerine and Fatty Acids (SREC-1), to promote extraction of part of the excess alcohol retained in (23), thereby preventing this alcohol from entering into contact with washing water in the washing system (SLAV-1) and becoming hydrated. This operation is carried out in one, two, three or four theoretical stages of intimate contact between the phases within the alcohol extraction system (SEXT-2).

The dense phase separated, rich in glycerine and alcohol with a low moisture content, is sent to the Section for Recovering Alcohols, Glycerine and Fatty Acids (SREC-1) (not shown) as (36), where the alcohol is recovered in anhydrous or semi-anhydrous form.

After extraction, phase (34), rich is biodiesel, is sent to the neutralization system (SN-1), where it is subjected to reaction with a neutralizing agent (16), and separation of the dense phase (17) and light phase (18) products of neutralization. The light phase, still constituted by crude, but neutralized, biodiesel with a lower alcohol content, passes to the washing system (SLAV-1) as (18), and the dense phase passes to the Section for Recovering Alcohols, Glycerine and Fatty Acids (SREC-1) as (17). From this point on, the process is the same as in FIG. 3.

The concept of the invention as described in the present specifications also includes the following additional observations.

In addition to reusing the catalyst contained in the dense phases separated after the various reaction steps, the present invention also offers the alternative of additional recovery of the catalyst by extracting the light phase flowing from the last reaction step with the dense phase flowing from the reactor, which operates without adding fresh catalyst.

Alternatively, the dense phase used for extraction can be pre-evaporated to remove excess alcohol, improving its capacity for extraction and decreasing the alcohol content of the light phase, which is passed to the purification steps.

The final washing of the biodiesel is performed using fresh water, which can be in counter current (in order to minimize consumption of water).

When the catalyst used in the transesterification reaction is of the basic type, the water can be pure or have a controlled pH in the range 1 to 7, and preferably between 3 and 7, and more preferably between 3 and 5.

The ideal number of washing stages depends on the type and purity of the oil, of the catalyst, of the alcohol, of the process conditions, of the route chosen for removing the excess alcohol, and the efficiency of removal and neutralization of excess catalyst. Typically this number varies from 1 to 7 stages for counter current washing—whatever is necessary and sufficient in order to remove the residual glycerine and soaps.

In addition, before washing with water the present invention allows for extraction of excess alcohol, using the glycerine leaving the system for recovering alcohols, glycerine and fatty acids. After the extraction, the biodiesel is passed to the normal washing steps and the glycerine returns to the system for recovering alcohols, thereby minimizing hydration of the alcohol, which occurs during washing of the biodiesel with water.

Also alternatively, before washing, whether or not it has been extracted with glycerine, the biodiesel can be submitted to preliminary evaporation in order to increase recovery of alcohol with a low water content.

The invention claimed is:

1. A process for producing biodiesel from natural oils and/or fats in the presence of a transesterification low molecular weight alcohol and a catalyst using a first reaction module (MR-1A) and a second reaction module (MR-1B) operating in parallel as a first reaction stage, and a third reaction module (MR-2) operating as a second reaction stage, comprising the following steps in continuous operation of reaction ((a) to (e)) and purification ((f) to (g)):

a) directing fresh oil or fat (1), fresh alcohol (2) and catalyst (3) to the first reaction module (MR-1A), without pre-mixing the fresh oil or fat (1), the fresh alcohol (2) or the catalyst (3), under process conditions of temperature from ambient temperature to 140° C., pressure from atmospheric pressure to 10 bars and a molar ratio of alcohol/(oil or fat) of 3 to 30, to mix, react, and separate a first dense phase (5), and a first light phase (4), formed during the reaction, wherein said first light phase (4) is rich in biodiesel, and said first dense phase (5) is rich in glycerine and includes catalyst;

b) directing fresh oil or fat (12), fresh alcohol (13) and a fraction (11) containing residual catalyst from the first reaction module (MR-1A) and the third reaction module (MR-2) to the second reaction module (MR-1B), without pre-mixing said fresh oil or fat (12), said fresh alcohol (13) or said fraction (11), mixing and reacting said fresh oil or fat (12), said fresh alcohol (13) and said fraction (11) under reaction conditions optionally similar to those in the first reaction module (MR-1A), and after the required reaction period separating the resulting product into a second dense phase (15) and a second light phase (8), wherein said second light phase (8) is rich in biodiesel, and said second dense phase (15) is rich in glycerine and includes catalyst;

c) directing said first light phase (4) rich in biodiesel, said second light phase (8) rich in biodiesel, fresh alcohol (6) and catalyst (7), to the third reaction module (MR-2), without pre-mixing said first light phase (4), said second light phase (8), said fresh alcohol (6) and said catalyst (7), reacting them under reaction conditions optionally similar to those of the first reaction module (MR-1A), and after the required reaction period separating the resulting products into a third dense phase (9) and a third light phase (10), wherein said third light phase is rich in biodiesel;

d) directing said third light phase (10) leaving the third reaction module (MR-2), sent as a phase (23), to a purification system (SP-1);

e) directing said second dense phase (15) separated in the second reaction module (MR-1B) and the excess, if any, of other dense phases (14), to a recovery system (SREC-1);

f) directing said third light phase (23) arriving at the purification system (SP-1) to a neutralization system (SN-1) where it reacts with a neutralizing agent (16), and then separating the resulting product into a fourth dense phase (17), which is directed to a recovery system (SREC-1) and a fourth light phase (18), which is directed to a washing system (SLAV-1);

g) removing water-soluble contaminants present in the light phase in the washing system (SLAV-1), with the help of water (37);

h) separating a fifth light phase (19) which leaves the washing system (SLAV-1), and directing it to a drying and wax removal system (SSRC-1), to obtain said biodiesel (21), and preferably directing separated aqueous phase (20) to the recovery system (SREC-1).

2. A process according to claim 1, alternatively comprising the following reaction steps (a) to (g):

a) directing, under process conditions of temperature from ambient temperature to 140° C., pressure from atmospheric pressure to 10 bars and a molar ratio of alcohol/(oil or fat) from 3 to 30, oil or fat (1), alcohol (2) and catalyst (3), to a first reaction module (MR-1A), to mix, react, and separate a first dense phase (5), and a first light phase (4), formed during the reaction;

b) directing oil or fat (12) and alcohol (13) to a second reaction module (MR-1B), together with a fraction (11) containing residual catalyst from the other reaction modules (MR-1A and MR-2), mixing and reacting said oil or fat (11), said alcohol (12), and said fraction (13) under reaction conditions preferably similar to those in the first reaction module (MR-1A), and after the required reaction period separating the resulting product into a second dense phase (15) and a second light phase (8);

c) directing the first and second light phases (4 and 8) to a third reaction module (MR-2), together with alcohol (6) and catalyst (7), mixing and reacting them under reaction conditions preferably similar to those of the first reaction module (MR-1A), and after the required period separating the resulting products into a third dense phase (9) and a third light phase (10);

d) directing the third light phase (10), the second dense phase (15) from the second reaction module (MR-1B) and a recycled dense phase (29) to a catalyst extraction system (SEXT-1), to obtain a fourth dense phase (28) and a fourth light phase (23);

e) directing the fourth light phase (23) to a purification system (SP-1);

f) directing one part of the fourth dense phase (28) to form a recycled dense phase (29) for the catalyst extraction system (SEXT-1), a second part to form a fifth dense phase (38) containing residual catalyst, and the remainder (30) to a recovery system (SREC-1);

g) directing any excess from the dense phases to the recovery system (SREC-1).

3. A process according to claim 2, additionally comprising the following alternative reaction steps:

a) passing the second dense phase (15, 31) through an alcohol evaporation/distillation system (SEVAP-2) and then directing a liquid phase (32) to a catalyst extraction system (SEXT-1);

b) directing alcohol removed (33) to a recovery system (SREC-1).

4. A process according to claim 1, comprising the following alternative purification steps:

a) directing the third light phase (23) to a neutralization system (SN-1), where it reacts with a neutralizing agent (16), and then separating the resulting products into a fourth dense phase (17) and a fourth light phase (18);

b) directing the fourth light phase (18), to an alcohol extraction system (SEXT-2), and the fourth dense phase (17) to a recovery system (SREC-1);

c) promoting in the alcohol extraction system (SEXT-2), with the aid of recovered glycerine (35), extraction of part of the excess alcohol retained in the fourth light phase (18), to prevent hydration of this alcohol by contact with water from the washing system (SLAV-1), thereby obtaining and separating a fifth dense phase (36), which is sent to a recovery system (SREC-I) to recover anhydrous or semi-anhydrous alcohol, and a fifth light phase (34);

d) directing the fifth light phase (34) to a washing system (SLAV-1), which also receives water (37), in order to remove water-soluble contaminants in said fifth light phase, and separating the resulting product into an aqueous phase (20), which is directed to a recovery system (SREC-1), and a sixth light phase (19);

e) directing the sixth light phase (19) to a drying and wax removal system (SSRC-1), from which said biodiesel (21) is recovered.

5. A process according to claim 1 comprising the following purification steps:
- a) directing the third light phase (23) to an alcohol extraction system (SEXT-2), which also receives recovered glycerine (35) from a recovery system (SREC-1), to promote extraction of part of the excess alcohol retained in the third light phase (23), to prevent hydration of the alcohol by contact with water from the washing system (SLAV-1), thereby obtaining a fourth dense phase (36) and a fourth light phase (34);
- b) separating and directing the fourth dense phase (36) to a recovery system (SREC-1) to recover anhydrous or semi-anhydrous alcohol;
- c) directing the fourth light phase (34) to a neutralisation system (SN-1) to react with a neutralizing agent (16), and then separating the resulting products into a fifth dense phase (17), which is directed to a recovery system (SREC-1), and a fifth light phase (18);
- d) directing the fifth light phase (18) to a washing system (SLAV-1), which also receives water (37), in order to remove water-soluble contaminants in said fifth light phase, and separating the resulting product into a sixth dense aqueous phase (20), which is directed to a recovery system (SREC-1), and a sixth light phase (19);
- e) directing the sixth light phase (19) to a drying and wax removal system (SSRC-1), from which said biodiesel (21) is recovered.

6. A process according to claim 1, wherein alternatively, before washing in a washing system (SLAV-1), a neutralised light phase (24) is submitted to an additional step of evaporation or distillation of excess alcohol, wherein said step includes directing said light phase to an evaporation/distillation system (SEVAP-1) to remove part or all of the residual alcohol content, separating and directing the alcohol removed (27) and a dense phase (26) to a recovery system (SREC-1), while a light phase (25) is sent to a washing system, (SLAV-1).

7. A process according to claim 1, wherein any dense phase (15, 17, 20, 22, 26, 27 and/or 36) arriving at the recovery system (SREC-1) enters this system at specific points in accordance with the contents of water therein and the decision to be adopted as to type of recovery.

8. A process according to claim 7, wherein the type of recovery involves premixing of the fractions or, alternatively separate treatment of the aqueous fractions, recovering all of the glycerine from the aqueous fractions or only treating them for disposal, converting the soaps in fatty acids and recovering the fatty acids or otherwise, and/or dehydrating the recovered alcohol or offering it for sale as hydrated alcohol (when the process uses ethyl alcohol), or any other combination.

9. A process according to claim 1, wherein said fresh oil and/or fat (1 and 12) comprises one or more natural oils selected from the group consisting of castor oil, pine nut oil, soybean oil, cottonseed oil, rapeseed oil, sunflower oil, and ouricoury palm oil and/or any natural fat, pure or mixed, virgin and/or reused.

10. A process according to claim 1, wherein said fresh alcohol (2, 6 and 13) is a pure $C_1$-$C_6$ alcohol or a mixture thereof.

11. A process according to claim 1, wherein said fresh alcohol (2, 6 and 13) is pure methanol or ethanol or a mixture thereof.

12. A process according to claim 1, wherein the molar ratio of alcohol/(oil or fat) fed to the first reaction module (MR-1A) is between 4 and 15.

13. A process according to claim 1, wherein the catalyst (3 and 7) is an acid or basic catalyst.

14. A process according to claim 13, wherein the proportion of basic catalyst to oil or fat is 0.1 to 2.5% by weight relative to the weight of oil or fat starting material in the unit.

15. A process according to claim 1, wherein if a basic catalyst is used for the transesterification reaction, the neutralizing agent can be any organic or inorganic acid, strong or weak, concentrated or dilute, in aqueous or alcoholic solution, as long as the turning point of the neutralization of the catalyst is carefully controlled.

16. A process according to claim 15, wherein the acids are one or more acids selected from the group consisting of hydrochloric, sulphuric, phosphoric, acetic and citric acids.

17. A process according to claim 15, wherein acidic buffers in the desired pH range are used to facilitate control.

18. A process according to claim 1, wherein if a basic catalyst is used in the transesterification reaction, the water for washing is pure or with pH controlled in the range between 1 to 7.

19. A process according to claim 18, wherein the pH of the water for washing is controlled in the range between 3 and 7.

20. A process according to claim 1, which includes three reaction steps, two reaction steps in parallel (R-1A and R-1B) using oil or fat as a starting material, and one reaction step in series (R-2) using as a starting material the light phases produced in the earlier reaction steps (R-1A and R-1B).

21. A process according to claim 20, wherein one of the two initial steps (R-1B) reuses the catalyst used in the other steps.

22. A process according to claim 21, wherein the reuse of the catalyst is accomplished by means of a fraction (11) which comprises totally or partially of first and third dense phases (5 and 9) separated in first and third reaction modules (MR-1A and MR-2).

23. A process according to claim 21, wherein said fraction (11) comprises first, third and fifth dense phases (5, 9, 38).

24. A process according to claim 1, wherein the third light phase (23) forwarded for purification is produced by any type of reaction process using an acid or basic catalyst.

\* \* \* \* \*